United States Patent [19]

Kimura et al.

[11] 4,201,872

[45] May 6, 1980

[54] PROCESS FOR PREPARING PURIFIED TEREPHTHALIC ACID

[75] Inventors: Tsuneo Kimura; Hiroshi Hashizume, both of Kita-Kyushu, Japan

[73] Assignee: Mitsubishi Chemical Industries Ltd., Tokyo, Japan

[21] Appl. No.: 713,825

[22] Filed: Aug. 12, 1976

[30] Foreign Application Priority Data

Aug. 26, 1975 [JP] Japan .............................. 50/103230

[51] Int. Cl.$^2$ .............................................. C07C 51/42
[52] U.S. Cl. .................................................. 562/487
[58] Field of Search ......................... 260/525; 562/487

[56] References Cited

U.S. PATENT DOCUMENTS

| 3,607,921 | 9/1971 | Stancell | 260/525 |
| 3,639,465 | 2/1972 | Olsen et al. | 260/525 |
| 3,862,218 | 1/1975 | Stautzenberger | 260/525 |

*Primary Examiner*—Alan Siegel
*Attorney, Agent, or Firm*—Oblon, Fisher, Spivak, McClelland & Maier

[57] ABSTRACT

A purified terephthalic acid is prepared by dissolving a crude terephthalic acid in water at high temperature under high pressure and then contacting the resulting aqueous solution with a catalyst of an active carbon supporting palladium under maintaining the pressure P(kg/cm$^2$) of the gaseous phase in the catalytic contacting zone in a range of $$P_o \leq P \leq P_o + 5$$

wherein Po represents a vapor pressure (kg/cm$^2$) of the aqueous solution at the reaction temperature, and then cooling the aqueous solution to crystallize terephthalic acid.

10 Claims, 2 Drawing Figures

PROCESS FOR PREPARING PURIFIED TEREPHTHALIC ACID

BACKGROUND OF THE INVENTION

The present invention relates to a process for preparing a purified terephthalic acid. More particularly, it relates to an improved process for preparing a purified terephthalic acid from a crude terephthalic acid obtained by a liquid phase oxidation of para-dialkylbenzene. In terephthalic acid obtained by a liquid phase air oxidation of paraalkylbenzene such as paraxylene, relatively large amounts of impurities such as 4-carboxybenzaldehyde(hereinafter referring to as 4-CBA) are included. These impurities adversely affect such polymerization reactions as the preparation of polyethyleneterephthalate which are present in the crude terephthalic acid which is used as the starting material. The impurities also cause the undesired coloring of the resulting polyethyleneterephthalate.

Accordingly, a need has existed for a method by which the impurities such as 4-CAB can be eliminated from the terephthalic acid. Various methods have been proposed for effecting the separation of 4-CBA from crude terephthalic acid. Among them, the method of purifying a crude terephthalic acid by contacting hydrogen with an aqueous solution of crude terephthalic acid in the presence of a catalyst to reduce 4-CBA to para-toluic acid or para-methylolbenzoic acid, which has certain advantages and is disclosed in USP al No. 3,584,039. The separation of para-toluic acid is easier than the separation of 4-CBA, however the former method also requirs special careful operation.

In another method of purifying terephthalic acid by separating impurities such as 4-CBA without the above-mentioned disadvantages, crude terephthalic acid which is obtained by the oxidation of p-dialkylbenzene is dissolved in water at high temperature under high pressure and then the aqueous solution of crude terephthalic acid is contacted with a catalyst of palladium on active carbon to yield a terephthalic acid product of high purity (hereinafter referred to as Pd/C catalyst) (Japanese Patent Publication No. 33189/1974).

According to said process, most of 4-CBA is converted to benzoic acid by a decarbonylation in the presence of the Pd/C catalyst, and the resulting benzoic acid has remarkably higher solubility in water than that of terephthalic acid and is easily removed by the crystallization. However, when the Pd/C catalyst is used for a long time, the catalytic activity is decreased to cause an imcomplete decomposition of the impurities such as 4-CBA and to remain the impurities in the resulting terephthalic acid. In order to prolong the life of the Pd/C catalyst, it is considered to use a crude terephthalic acid having higher purity or to increase an amount of the Pd/C catalyst.

However, these considerations are disadvantageous in industrial operations. Through further studies it has now been found that in the process a contacting crude terephthalic acid with the Pd/C catalyst, carbon monoxide which is formed by the reaction, is dissolved in the liquid phase and the catalyst is poisoned by the dissolved carbon monoxide which results in a decrease in catalyst activity for the decomposition of 4-CBA and which shortens the life of the catalyst. It has also been found that the carbon monoxide, which is dissolved in the liquid phase, can be removed from the liquid phase to the gaseous phase by decreasing the pressure in the catalyst contacting step thereby prolonging the lifetime of the catalyst.

SUMMARY OF THE INVENTION

It is an object of the present invention to provide a process for preparing a purified terephthalic acid by contacting an aqueous solution of crude terephthalic acid with a Pd/C catalyst in long catalytic life.

The object of the invention has been attained by producing a purified terephthalic acid by dissolving a crude terephthalic acid, which is obtained by a liquid phase oxidation of para-dialkylbenzene, in water at high temperature under high pressure and contacting the aqueous solution of crude terephthalic acid with a catalyst of an active carbon supporting palladium under maintaining the pressure P ($kg/cm^2$) of the gaseous phase in the catalytic contacting zone in a range of $Po \leq P \leq Po + 5$ wherein Po represents a vapor pressure ($kg/cm^2$) of the aqueous solution at the reaction temperature; and then cooling the aqueous solution to crystallize purified terephthalic acid.

Figure 1:
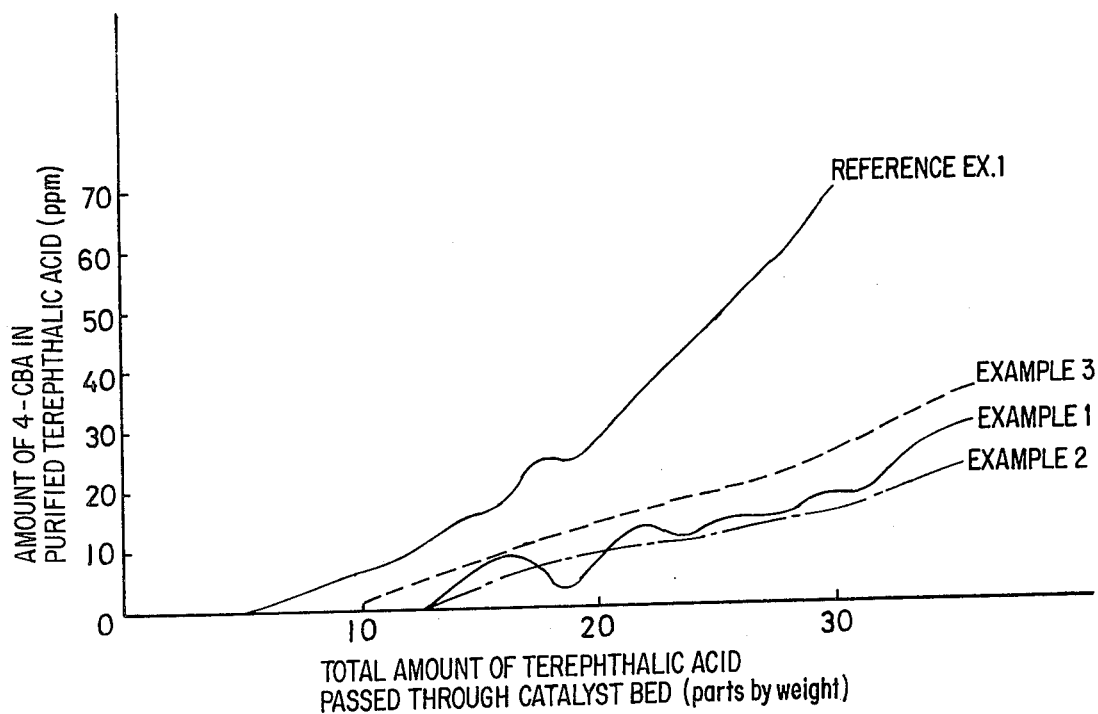
FIG. 1 is a graph showing the amount of 4-CBA in purified terephthalic acid (ppm) versus the total amount of terephthalic acid which passes through a catalyst bed.

DETAILED DESCRIPTION OF THE PREFERRED EMBODIMENTS:

According to the known process, the crude terephthalic acid can be produced by a liquid phase oxidation of para-dialkylbenzene in the presence of a heavy metal catalyst (USP al No. 2,833,816).

The crude terephthalic acid usually contains higher than 1000 ppm of 4-CBA.

In the process of the present invention the temperature at which the aqueous solution of crude terephthalic acid is contacted with the Pd/C catalyst should be less than the critical temperature of water in order than an aqueous solution of crude terephthalic acid the maintained in the reactor without boiling. Preferably, the temperature is maintained in the range of 200° C. to 320° C. especially 230° C. to 290° C. upon consideration of the solubility characteristics of terephthalic acid in water and the inhibition of thermal cracking of terephthalic acid.

The concentration of terephthalic acid in water is decided by the solubility of terephthalic acid in water and is usually in a range of 10 to 30 wt. % for an industrial operation. The catalytic contact of the aqueous solution of crude terephthalic acid of the invention can be carried out by passing the aqueous solution of crude terephthalic acid through a fixed bed which is prepared by packing the Pd/C catalyst. The pressure within the reactor in the contact of the solution with the catalyst should be higher than the vapor pressure of the aqueous solution so as to maintain the aqueous solution of crude terephthalic acid in liquid form and should be in a specific range. That is, it is necessary to maintain the pressure P in the catalytic contacting step in a range of $Po \leq P \leq Po + 5$ preferably $Po \leq P \leq Po + 3$ wherein Po represents a vapor pressure ($kg/cm^2$) of the aqueous solution of crude terephthalic acid at the reaction temperature.

When the pressure is higher than said range, carbon monoxide dissolved in the aqueous solution substantially remained in the liquid phase without vaporizing whereby the Pd/C catalyst is poisoned and the life of the catalyst can not be prolonged. The pressure P can be maintained at the predetermined pressure by continuously feeding an inert gas such as nitrogen, carbon, dioxide, argon, helium etc. and continuously purging the inert gas and the accompanied steam and carbon monoxide etc. by a pressure control device.

In another method of controlling the pressure without feeding an inert gas into the reactor, the pressure P of the gaseous phase can be maintained at the predetermined pressure by continuously purging carbon monoxide and steam generated within the aqueous solution from the reactor at a rate such that the pressure P is maintained within the desired range. In the operation of the latter method in which the pressure of the gaseous phase is maintained the same as the vapor pressure of the aqueous solution, it is necessary to prevent the discharge of the gases at a high rate from the pressure control device so as to prevent bumping of the solution during purging. The purged steam can be obtained from the steam which is formed by operation of stem from the surface of the aqueous solution thereby preventing bumping. Suitable Pd/C catalysts include various catalysts in which the Pd component is supported on carbon substrates such as active carbon in amounts of preferably 0.6 to 10 wt. % of Pd. The Pd/C catalyst can be prepared by immersing an active carbon obtained from charcoal, coconut shell coal or coal in a solution prepared by dissolving palladium chloride in hydrochloric acid, and then drying and crushing and reducing it in a solvent with formic acid, formaline hydrogen etc.

Figure 2:
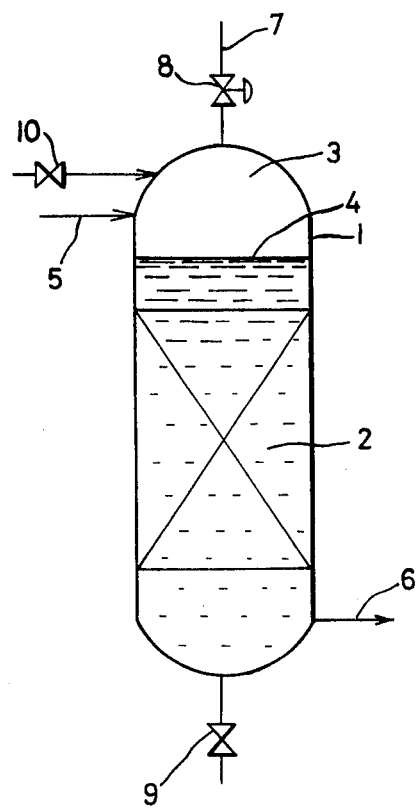
FIG. 2 is a diagram of an embodiment of the reactor of the present invention.

The temperature for crystallizing terephthalic acid from the aqueous solution is dependent upon the concentration of terephthalic acid in the aqueous solution of terephthalic acid, the reaction temperature, and the recovering ratio of terephthalic acid, and is usually lower than 100° C. in the conventional method. When the temperature for crystallizing terephthalic acid is higher than 140° C., terephthalic acid having specially high purity can be obtained. As indicated above the essential feature of the present process is that the life of the catalyst can be prolonged and the 4-CBA impurity can be effectively removed from the product for long periods of time in the process to produce a pure terephthalic acid from the crude terephthalic acid. An embodiment of the process of the invention can be better understood by reference to FIG. 2.

In reactor (1) having a fixed bed (29 of a Pd/C catalyst a heated aqueous solution of crude terephthalic acid is continuously fed through inlet pipe (5) and the treated aqueous solution of terephthalic acid is discharged from the outlet pipe (6) while maintaining the level (4) of aqueous solution above the fixed bed (2).

An inert gas of nitrogen is continuously fed through an inlet pipe (10) in order to maintain the pressure in the free gas zone (3) within the range of $Po \leq P \leq Po+5$ while purging the gases from the free gas zone through outlet pipe (7) equipped with pressure control valve (8). The aqueous solution can be discharged from the bottom of the reactor (1) through outlet pipe (9) which is equipped with a valve which is closed under normal conditions.

In the other embodiment, the inlet pipe (10) is closed, and steam generated from the heated aqueous solution of crude terephthalic acid, is particularly purged together with CO gas through the outlet pipe (7). The temperature of the aqueous solution in the reactor is maintained at a desired temperature in a range of 200 to 320° C.

The pressure control value (8) can be sensitive for controlling the pressure in the gaseous phase.

Having generally described the invention, a further understanding can be obtained by reference to certain examples which are provided herein for purposes of illustration only and are not intended to be limiting in any manner unless otherwise specified.

EXAMPLE 1

In a reactor made of titanium metal, 0.015 wt. part of a Pd/C catalyst (supporting 2.0 wt. % of Pd) was packed and 20% aqueous solution of a crude terephthalic acid containing 2000 ppm of 4-CBA which was obtained by a liquid phase oxidation of paraxylene was passed through the reactor at a space velocity of $6 \text{ hr}^{-1}$ at 275° C. The vapor pressure of the 20% aqueous solution of crude terephthalic acid was 62 atm. Gauge (63 kg/cm$^2$). Nitrogen gas was fed to the gaseous phase of the reactor and the pressure in the reactor was maintained to be 63 atm. Gauge (64 kg/cm$^2$) with a pressure control valve by purging the gases.

The resulting aqueous solution of terephthalic acid was cooled to 100° C. to crystallize terephthalic acid. The terephthalic acid crystals were separated from the mother liquor and was dried at 100° C. for more than 10 hours.

The result of analysis of carbon monoxide in the gase obtained by separating moixsture from the gas purged from the reactor, as shown in Table 1. The relation of total amounts of terephthalic acid passed through catalyst bed to an amount of 4-CBA remained in purified terephthalic acid is shown in FIG. 1.

EXAMPLE 2

The process of Example 1 was repeated except continuously purging a part of steam generated from the aqueous solution without feeding nitrogen gas so as to maintain the total pressure to 62 atm. Gauge. (63 kg/cm$^2$).

The relation of total amounts of terephthalic acid passed through catalyst bed to an amount of 4-CBA remained in purified terephthalic acid is shown in FIG. 1.

EXAMPLE 3

The process of Example 1 was repeated except continuously feeding nitrogen gas to the reactor and continuously purging the gases with the pressure control valve to maintain the total pressure to 65 atm. Gauge (66 kg/cm$^2$). The result of the analysis of carbon monoxide in the gas obtained by separating moisture from the gas purged from the reactor is shown in Table 1.

The relation of total amounts of terephthalic acid passed through catalyst bed to an amount of 4-CBA remained in purified terephthalic acid is shown in FIG. 1.

Reference

The process of Example 1 was repeated except maintaining the total pressure to 69 atm. Gauge (70 kg/cm$^2$). The result of the analysis of carbon monoxide in the gas obtained by separating moisture from the gas purged from the reactor is shown in Table 1.

The relation of total amounts of terephthalic acid passed through catalyst bed to an amount of 4-CBA remained in purified terephthalic acid is shown in FIG. 1.

Table 1

| Example | Exp. 1 | Exp. 2 | Exp. 3 | Reference |
| --- | --- | --- | --- | --- |
| Analytical value* of CO (mol %) | 3.8 | ** | 3.2 | 0.1 |
| CO in purged gas/ calculated CO based on decomposition of 4-CBA | 0.61 | ** | 0.52 | 0.02 |

Note:
*Measurement of CO content: A gas purged was passed through a cooling condenser to separate moisture and the dried gas was sampled and fed to a gas chromatrograph (Shimazu G.C-3A manufactured by Shimazu Seisakusho K.K.) at 40 to 50° C. with a carrier gas of argon.
**The measurement could not be carried out. The purged gas mostly contained steam whereby it was impossible to measure CO content by a gas chromatography.

What is claimed as new and intended to be secured as Letters Patent is:

1. A process for purifying terephthalic acid which is obtained by liquid phase oxidation of p-dialkylbenzene in water at high temperature under high pressure, which consists essentially of:
contacting an aqueous solution of crude terephthalic acid obtained from the oxidation step with a catalyst of palladium supported on active carbon to effect decarbonylation of the 4-carboxybenzaldehyde impurity in the crude terephthalic acid under the pressure of an ambient atmosphere comprising steam and carbon monoxide in the range of $Po \leq P \leq Po+5$, said carbon monoxide present being only derived by the decarbonylation of said 4-carboxybenzaldehyde, wherein Po represents the vapor pressure (kg/cm$^2$) of the aqueous solution at the reaction temperature of 200° C. to 320° C.; and
cooling the solution to effect separation by crystallization of pure terephthalic acid from solution thereby leaving water soluble impurities comprising benzoic acid formed by said decarbonylation in said solution.

2. The process of claim 1 wherein the pressure P of the gaseous phase in the catalyst contacting zone is in the range of $$Po \leq P \leq Po+3$$

3. The process of claim 1 wherein an inert gas is continuously fed into said reactor and the mixed inert gas, steam and carbon monoxide are continuously purged from the reactor while maintaining the pressure in the gaseous phase in a range of $$Po \leq P \leq Po+5$$

4. The process of claim 3, wherein said inert gas is nitrogen, carbon dioxide, argon or helium.

5. The process of claim 1, wherein the gaseous phase is principally steam and the steam and carbon monoxide are continuously purged from the reactor whiie maintaining the pressure in the gaseous phase in a range of $$Po \leq P \leq Po+5$$

6. The process of claim 1, wherein said aqueous solution of crude terephthalic acid has a concentration of 10 to 30 wt. %.

7. The process of claim 1, wherein the aqueous solution of crude terephthalic acid is continuously passed through a fixed bed of said catalyst while maintaining the pressure in the range of $$Po \leq P \leq Po+5$$

thereby purging gases from said reactor.

8. The process of claim 7 wherein the aqueous solution of crude terephthalic acid is passed through a fixed bed of a catalyst of 0.6 to 10 wt. % palladium supported on active carbon.

9. The process of claim 1, wherein said solution of crude terephthalic acid is contacted with said catalyst at a temperature of 230° C. to 290° C.

10. The process of claim 1, wherein the concentration of terephthalic acid in said solution of crude terephthalic acid ranges from 10 to 30 wt. %.

* * * * *